United States Patent [19]

Usui et al.

[11] Patent Number: 5,166,064
[45] Date of Patent: Nov. 24, 1992

[54] IMMOBILIZED OF LIPASE ON A CATION EXCHANGE RESIN

[75] Inventors: Naoki Usui; Naoto Kato, both of Kawasaki; Joji Takahashi, 4-46-13, Sakuragaoka, Tama-shi, Tokyo, all of Japan

[73] Assignees: Ajinomoto Co., Inc.; Joji Takahashi, both of Tokyo, Japan

[21] Appl. No.: 554,877

[22] Filed: Jul. 20, 1990

[30] Foreign Application Priority Data

Jul. 31, 1989 [JP] Japan .................. 1-198473

[51] Int. Cl.$^5$ ............... C12N 11/08; C12N 9/20; C12P 1/64
[52] U.S. Cl. .................... 435/180; 435/134; 435/198
[58] Field of Search ........... 435/134, 174, 177, 180, 435/198

[56] References Cited

U.S. PATENT DOCUMENTS

| | | | |
|---|---|---|---|
| 4,416,991 | 11/1983 | Matsuo et al. | 435/134 |
| 4,472,503 | 9/1984 | Matsuo et al. | 435/176 |
| 4,518,695 | 5/1985 | Hasegawa | 435/206 |
| 4,798,793 | 1/1989 | Eigtved | 435/134 |
| 4,818,695 | 4/1989 | Eigtved | 435/134 |
| 5,061,498 | 10/1991 | Matsuzaki et al. | 435/134 X |

FOREIGN PATENT DOCUMENTS

| | | |
|---|---|---|
| 98984 | 6/1985 | Japan . |
| 202688 | 9/1986 | Japan . |
| 22795 | 5/1988 | Japan . |

Primary Examiner—David M. Naff
Attorney, Agent, or Firm—Oblon, Spivak, McClelland, Maier & Neustadt

[57] ABSTRACT

An immobilized lipase is prepared by adsorbing lipase on a carrier that is capable of retaining 3% or more by weight of water after drying under a reduced pressure of from 0.01 to 1.0 Torr at 70° C. for 60 hours. A cation exchange resin is a preferred carrier and a weakly acidic cation exchange resin is most preferred. The lipase adsorbed on the carrier can be a freeze dried lipase and the resultant carrier-adsorbed lipase is dried. Lecithin may be adsorbed on the carrier as an enzyme activity enhancing agent. The immobilized lipase may also contain a dispersing agent. The immobilized lipase can be used for modifying fats and oils.

22 Claims, No Drawings

IMMOBILIZED OF LIPASE ON A CATION EXCHANGE RESIN

BACKGROUND OF THE INVENTION

1. Field of the Invention

The present invention relates to an immobilized lipase preparation used for modifying fats and oils and to a process for the preparation thereof.

2. Description of the Prior Art

A method for modifying fats and oils using an immobilized lipase preparation has hitherto been known. The immobilized lipase preparation is obtained by adsorbing lipase on a carrier. As the carrier, inorganic carriers such as Celite, pig bone, diatomaceous earth or kaolinite are generally known. Further, a synthetic adsorbing agent such as an anion exchange resin is known (see e.g. Japanese Patent Unexamined Published Applications Nos. 61-202688 and 60-98984). However, these immobilized lipase preparations heretofore known have the problem that it is difficult to maintain their enzyme activity for a long period of time.

SUMMARY OF THE INVENTION

Thus, an object of the present invention is to provide an immobilized lipase preparation which is capable of maintaining its enzyme activity for a long period of time.

A second object of the present invention is to provide a process for preparing an immobilized lipase preparation which is capable of maintaining its enzyme activity for a long period of time.

The above-mentioned objects are attained by using a material having a water retention of 3% by weight or more, as a carrier. Namely, the present invention provides an immobilized lipase preparation which comprises a lipase adsorbed on a carrier having a water retention of 3% by weight or more. Further, the present invention provides a process for preparing an immobilized lipase preparation which comprises mixing a lipase solution with a carrier having a water retention of 3% by weight or more to adsorb the lipase on the carrier, and drying the resulting carrier-adsorbed lipase.

Further objects, features and advantages of the present invention will become apparent from the Detailed Description of Preferred Embodiments which follows.

DETAILED DESCRIPTION OF THE PREFERRED EMBODIMENTS

The term "water retention" according to the present invention means the water content of a carrier after drying the carrier under reduced pressure of from 0.01 to 1.0 Torr, at 70° C. for 60 hours.

As the lipase used for the lipase preparation, for example, there may be included those derived from plant seeds such as sunflower seed or rape seed; mold; yeast and bacteria; and commercially available freeze-dried lipase products having high hydrolytic activity may also be preferably used.

As the carrier, there may usually be used any material having a water retention of 3% by weight or more. Preferred are weakly acidic or strongly acidic cation exchange resins, the weakly acidic cation exchange resins being more preferred. The examples include carboxylic acid-type cation exchange resins WK-13 and WK-11 manufactured by Mitsubishi Chemical Industries, Ltd.

In the present invention, a single carrier may be used alone, or two or more kinds of carriers may be used in combination. If a plurality of carriers is used, each carrier does not necessarily have to have a water retention of 3% by weight or more, so long as the entire composite carrier made of a plurality of carriers has a water retention of 3% by weight or more.

When an enzyme activating agent and/or other enzyme activity enhancing agent to be adsorbed on the carrier have a water retention properties, such agents also contribute to the water retention of the resulting carrier. In such a case, the water retention of the resulting carrier may include that of such agents.

The lipase preparation may be prepared, following known methods, e.g. by immersing 100 parts by weight of a carrier into from 20 to 200 parts by volume of a lipase solution, and then drying the resulting carrier-adsorbed lipase under reduced pressure of from 0.01 to 100 Torr for 1 to 24 hours. The amount of lipase adsorbed on the carrier is suitably in the range of from 0.001 to 0.1 part by weight per part by weight of the carrier. In addition to lipase, an enzyme activity enhancing agent such as lecithin may also be used. The amount of lecithin to be added is suitably in the range of from 0.001 to 0.1 part by weight per part by weight of the carrier.

In the preparation of the lipase preparation, an alcohol, acetone, glycerol, fats and oils, hexane, surfactants, etc. or a suitable combination of the above may be added to enhance dispersion of lipase and optional lecithin into water.

The lipase preparation according to the invention can be effectively used for modifying plant oils such as sesame oil, rapeseed oil, cottonseed oil, soybean oil, camellia oil, olive oil, castor oil, coconut oil or palm oil; marine animal oils such as sardine oil, herring oil, saury oil, shark oil or whale oil; land animal oils such as tallow or lard; or mixtures of the above.

An ester interchange reaction may be carried out in an inert gas atmosphere such as under nitrogen gas, or under reduced pressure. The reaction temperature is suitably in the range of from 20° to 80° C. and the reaction time is suitably in the range of from 1 to 30 hours. The amount of the lipase preparation to be added to raw oil is suitably from 1 to 20 parts by weight based on 100 parts by weight of the raw oil.

If water is present during the ester interchange reaction or the ester synthetic reaction, the yield of triglycerides is reduced and the reaction rate decreases. In order to avoid such disadvantages, it is preferable to preliminarily dehydrate the raw oil and the reaction substrate by means of a vacuum dryer so that the water content in the reaction system becomes 200 ppm or less, particularly 100 ppm or less. For dehydration, it is also advisable to add a dehydrating agent such as Molecular Sieve 3A to the raw oil.

EXAMPLE

As a lipase, a freeze-dried sample of lipase derived from

Rhizopus delemar (manufactured by Amano Pharmaceutical Co. Ltd., hydrolytic activity: 3000 U/mg) was used. The sample was dissolved in water to prepare a lipase solution (13.3 mg/ml), and then an activity enhancing agent, i.e., lecithin, was added to the solution in a concentration of 4 mg/ml. In preparing the nine examples listed in Table 1, four grams of each of Celite 535 (manufactured by Manvill Co. Ltd.), a cation exchange resin WK-13 (manufactured by Mitsubishi Chemical Industries, Ltd.), a cation exchange resin WK-11 (manufactured by Mitsubishi Chemical Industries, Ltd.), an anion exchange resin SA-10AS (manufactured by Mitsubishi Chemical Industries, Ltd.), an anion exchange resin HPA-25 (manufactured by Mitsubishi Chemical Industries, Ltd.), a chelate resin CR-20 (manufactured by Mitsubishi Chemical Industries, Ltd.), an adsorptive resin HP-2MG (manufactured by Mitsubishi Chemical Industries, Ltd.), an adsorptive resin HP-10 (manufactured by Mitsubishi Chemical Industries, Ltd.) or adsorptive resin HP-20 (manufactured by Mitsubishi Chemical Industries, Ltd.) was added to 4 ml of the solution. Each resulting mixture was then dried at 40° C., at 60 Torr or less for 16 to 18 hours to prepare a lipase preparation.

Rapeseed oil and crude palm olein (weight ratio: 50:50) were subjected to dehydration under reduced pressure at 80° C., at 20 Torr for 20 minutes, thereby reducing the water content to 200 ppm or less. Molecular Sieve 3A (manufactured by Union Showa Co. Ltd.) was added to the fats and oils in an amount of 10% by weight based on the weight of the fats and oils. The resulting fats and oils were subjected to a subsequent modification.

Three grams of the lipase preparation was packed into a column The reaction was carried out by passing the fats and oils mixture to the column at a flow rate of 3.3 g/hr while carefully preventing the fats and oils from absorbing water, and by heating the entire apparatus to 60° C. A half-life of activity of each lipase preparation is listed in Table 1.

TABLE 1

| Carrier | Activity Half-life (hr) | Water Retention (Wt. %) | |
|---|---|---|---|
| Celite | 85 | 0.3 | Comparative Example |
| WK-13 | 126 | 3.4 | Example |
| WK-11 | 120 | 3.1 | Example |
| SA-10AS | 99 | 2.1 | Comparative Example |
| HPA-25 | 98 | 2.1 | Comparative Example |
| CR-20 | 36 | 2.7 | Comparative Example |
| HP-2MG | 36 | 2.4 | Comparative Example |
| HP-10 | 55 | 1.6 | Comparative Example |
| HP-20 | 36 | 1.5 | Comparative Example |

As is seen from Table 1, in case of using the carrier WK-13, a half-life of activity of which is the longest among the carriers, the yield of triglycerides after 16 hours was 99% or more.

As is understood from the foregoing general description and specific examples, the immobilized lipase preparation according to the present invention maintains enzyme activity for a long period of time. Accordingly, by using the immobilized lipase preparation, it is possible to continuously carry out an operation for modifying fats and oils for a long period of time.

The present invention has been illustrated by several non-limiting examples. One of ordinary skill in the art will recognize, however, that modifications and improvements may be made while remaining within the scope of the present invention as recited in the appended claims.

What is claimed is:

1. An immobilized lipase preparation which comprises a lipase absorbed on a carrier, wherein said carrier is a cation exchange resin and said carrier has a water content of 3% or more by weight after said carrier has been dried under reduced pressure of from 0.01 to 1.0 Torr, at 70° C. for 60 hours.

2. The lipase preparation of claim 1, wherein the lipase is a freeze-dried lipase.

3. The lipase preparation of claim 1, wherein the carrier is a weakly acidic cation exchange resin.

4. The lipase preparation of claim 1, wherein the amount of lipase to be adsorbed on the carrier is in the range of from 0.001 to 0.1 part by weight per part by weight of the carrier.

5. The lipase preparation of claim 1, which further comprises lecithin as an enzyme activity enhancing agent to be adsorbed on the carrier.

6. The lipase preparation of claim 5, wherein the amount of lecithin to be adsorbed on the carrier is in the range of from 0.001 to 0.1 part by weight per part by weight of the carrier.

7. The lipase preparation of claim 1, which further comprises a dispersing agent.

8. The lipase preparation of claim 7, wherein the dispersing agent is one or more agents selected from the group consisting of an alcohol, acetone, glycerol, oils and hexane.

9. The lipase preparation of claim 7 wherein the dispersing agent is a surfactant.

10. The lipase preparation of claim 8 wherein the sil is a fat.

11. A process for preparing an immobilized lipase preparation, which comprises mixing a lipase solution with a carrier and drying the resulting carrier-absorbed lipase, wherein said carrier is a cation exchange resin and has a water content of 3% or more by weight after said carrier has been dried under reduced pressure of from 0.01 to 1.0 Torr, at 70° C. for 60 hours.

12. The process of claim 11, wherein 100 parts by weight of the carrier is immersed into from 20 to 200 parts by volume of the a lipase solution.

13. The process of claim 11, wherein drying the carrier-adsorbed lipase is carried out under reduced pressure of from 0.01 to 100 Torr for 1 to 24 hours.

14. The process of claim 11, wherein the lipase is a freeze-dried lipase.

15. The process of claim 11, wherein the carrier is a weakly acidic cation exchange resin.

16. The process of claim 11, wherein the amount of lipase adsorbed on the carrier is in the range of from 0.001 to 0.1 part by weight per part by weight of the carrier.

17. The process of claim 11, wherein the lipase solution further comprises lecithin as an enzyme activity enhancing agent.

18. The process of claim 17, wherein the amount of lecithin to be adsorbed on the carrier is in the range of from 0.001 to 0.1 part by weight per part by weight of the carrier.

19. The process of claim 11, wherein the lipase solution further comprises a dispersing agent.

20. The process of claim 19, wherein the dispersing agent is one or more agents selected from the group consisting of an alcohol, acetone, glycerol, oils and hexane.

21. The process of claim 19 wherein the dispersing agent is a surfactant.

22. The process of claim 20 wherein the oil is a fat.

* * * * *

UNITED STATES PATENT AND TRADEMARK OFFICE
CERTIFICATE OF CORRECTION

PATENT NO. : 5,166,064

DATED : November 24, 1992

INVENTOR(S) : Usui, et al.

It is certified that error appears in the above-identified patent and that said Letters Patent is hereby corrected as shown below:

In the title on the title page and in column 1, line 2, delete "IMMOBILIZED" and insert --IMMOBILIZATION--.

In column 2, line 10, after "have", delete -- a --.

In column 2, line 61, "Rhizopus delemar" should be in italics.

In column 3, line 27, after "column" insert --. --.

In column 4, line 27, delete "sil" and insert --oil--.

Signed and Sealed this

Thirtieth Day of November, 1993

Attest:

Attesting Officer

BRUCE LEHMAN

Commissioner of Patents and Trademarks